United States Patent [19]
Lewis et al.

[11] Patent Number: 5,902,235
[45] Date of Patent: May 11, 1999

[54] OPTICAL CEREBRAL OXIMETER

[75] Inventors: Gary D. Lewis, St. Clair Shores; Wayne P. Messing, Troy; Melville C. Stewart, II, Ann Arbor, all of Mich.

[73] Assignee: Somanetics Corporation, Troy, Mich.

[21] Appl. No.: 08/584,147

[22] Filed: Jan. 8, 1996

Related U.S. Application Data

[63] Continuation of application No. 08/361,180, Dec. 21, 1994, abandoned, which is a continuation of application No. 08/161,502, Dec. 2, 1993, abandoned, which is a continuation of application No. 08/006,705, Jan. 21, 1993, abandoned, which is a continuation of application No. 07/711,147, Jun. 6, 1991, abandoned, which is a continuation-in-part of application No. 07/329,945, Mar. 29, 1989, Pat. No. 5,139,025.

[51] Int. Cl.$^6$ ................................................ A61B 5/00
[52] U.S. Cl. .................... 600/323; 600/324; 600/473; 600/476
[58] Field of Search ..................... 128/633, 664–5; 356/41; 600/310–322, 320, 473–478

[56] References Cited

U.S. PATENT DOCUMENTS

| | | |
|---|---|---|
| 3,638,640 | 2/1972 | Shaw . |
| 4,223,680 | 9/1980 | Jöbsis ................................... 128/633 |
| 4,281,645 | 8/1981 | Jöbsis ................................... 128/633 |
| 4,321,930 | 3/1982 | Jöbsis ................................... 128/633 |
| 4,380,240 | 4/1983 | Jöbsis ................................... 128/633 |
| 4,485,820 | 12/1984 | Flower . |
| 4,510,938 | 4/1985 | Jöbsis ................................... 128/633 |
| 4,570,638 | 2/1986 | Stoddart et al. ....................... 128/665 |
| 4,807,631 | 2/1989 | Hersh et al. ............................. 356/41 |
| 4,901,238 | 2/1990 | Suzuki ................................... 128/633 |
| 4,907,876 | 3/1990 | Suzuki ................................... 128/633 |
| 4,908,762 | 3/1990 | Suzuki ................................... 128/633 |
| 5,419,321 | 5/1995 | Evans . |
| 5,524,617 | 6/1996 | Mannheimer .......................... 600/323 |

FOREIGN PATENT DOCUMENTS

| | | |
|---|---|---|
| A30286142 | 10/1988 | European Pat. Off. . |
| 0290278 | 11/1988 | European Pat. Off. ............... 128/633 |
| A10290279 | 11/1988 | European Pat. Off. . |

OTHER PUBLICATIONS

Noninvasive measurement of Regional Cerebrovascular oxygen saturation in humans using optical spectroscopy By Patrick W. McCormick, Melville Stewart, Gary Lewis.

*Primary Examiner*—Robert L. Nasser
*Attorney, Agent, or Firm*—Price, Heneveld, Cooper, DeWitt & Litton

[57] ABSTRACT

A spectrophotometric instrument for conducting in vivo patient examinations has a sensor which is applied to the patient target area, e.g. the forehead, which includes a source for emitting electromagnetic energy e.g. selected wavelengths in the near infrared range, such that the energy passes through the underlying tissue and is emitted at other locations spaced from the point of entry. The sensor also includes detectors for receiving the resulting light energy at two or more such other locations and sending corresponding signals to a processor for analysis, by which characteristics of the tissue transmitted by the examination wavelengths may be determined. Processing of such signals includes the contrasting of detected intensity levels corresponding to a reference wavelength received at one detection location with intensity signals representative of an investigative wavelength also received at such location to determine a first resultant signal, repeating the process for the same wavelengths at another detection location, to thus determine another resultant signal, and the contrasting of such two resultant signals. In a particular application, the instrument is used to determine regional cerebral blood oxygenation by processing the detection signals to obtain a first resultant having a value proportional to the ratio of deoxygenated hemoglobin with respect to oxygenated hemoglobin and then using the value of such resultant to compute a further resultant having a value proportional to the ratio of oxygenated hemoglobin with respect to the sum of oxygenated hemoglobin and deoxygenated hemoglobin.

19 Claims, 5 Drawing Sheets

OPTICAL CEREBRAL OXIMETER

CONTINUING AND RELATED DATA

This application is a continuation of U.S. application Ser. No. 08/361,180, filed Dec. 21, 1994, now abandoned, which is a continuation of U.S. application Ser. No. 08/161,502, filed Dec. 2, 1993, now abandoned, which is a continuation of U.S. application Ser. No. 08/006,705, filed Jan. 21, 1993, now abandoned, which is a continuation of U.S. application Ser. No. 07/711,147, filed Jun. 6, 1991, now abandoned, which is related to and is a continuation-in-part of U.S. application Ser. No. 07/329,945, filed Mar. 29, 1989, now U.S. Pat. No. 5,139,025. This application is also related to U.S. application Ser. Nos. 07/830,567, filed Feb. 18, 1986, now U.S. Pat. No. 4,768,516, and is related to U.S. application Ser. No. 06/830,578, filed Feb. 18, 1986, now U.S. Pat. No. 4,817,623, and is related to U.S. application Ser. No. 06/827,526, filed Feb. 10, 1986, now U.S. Pat. No. 5,140,989, and is related to U.S. application Ser. No. 06/542,022, filed Oct. 14, 1993, now U.S. Pat. No. 4,570,638, the disclosures of which are each incorporated by reference herein.

TECHNICAL FIELD

This invention relates generally to in vivo spectrophotometric methods and apparatus, for examining and/or monitoring biological tissue, substances and/or conditions in living subjects, in particular humans. More particularly, the invention relates to the novel application of such in vivo methods and apparatus to provide a new form of biomedical device for non-invasively monitoring oxidative metabolism in mammalian (e.g. human) subjects on an in vivo basis, a specific and preferred embodiment of which comprises means for so-monitoring regional oxygen saturation in the brain, and for providing a quantitative readout thereof in terms familiar to medical practitioners, i.e., percent oxygen saturation.

BACKGROUND

Spectrophotometry has, of course, long been used as a valuable investigative tool in various scientific fields, particularly biological and medical research, and various applications of the underlying principles utilizing selected wavelengths of light in the near infrared range (often referred to as N.I.R. spectrophotometry) have for quite some time been utilized for certain in vivo procedures and/or investigation on human beings. For example, a frequently-encountered such device is the pulse oximeter conventionally used in hospitals and other medical facilities to provide a direct indication of arterial oxygen saturation by means of a clip or the like which fastens to an appendage such as the ear or finger of the patient. As has been noted by a small but growing field of investigators, the potentially useful applications of N.I.R. in vivo spectrophotometry are considerably broader and more diverse than this, however, due to the interesting and useful characteristic of N.I.R. wavelengths in being able to pass through ("transmiss") biological substance such as human skin, bone, and tissue for at least a length of several centimeters, and a useful brief description and commentary as to this is set forth in the above-referenced prior applications and/or patents attributable in at least part to the present inventor (see for example U.S. Pat. No. 4,570,638), as well as in the various references of record therein. In the latter regard, particular reference is made to the patents issued to Jobsis et al, e.g. U.S. Pat. Nos. 4,281,645, 4,223,680 and 4,321,930.

While previous developments in the general field of N.I.R. in vivo spectrophotometry, as noted above, have no doubt provided interesting and at least potentially useful insights and information heretofore, many important further developments and applications no doubt remain to be made, and certain of these are likely to be of considerable importance to medical practitioners. For example, accurate, meaningful, non-intrusive monitoring of brain status and viability is a most important need which prior technology has not sufficiently satisfied. As is well known and widely appreciated, the brain is a delicate and easily-damaged portion of human anatomy, while at the same time being the epicenter of neurological and physiological function. Brain damage through injury or cerebral vascular disease is responsible for numerous deaths and serious illnesses each year, involving on the order of at least 100,000 surgical procedures annually in recent years. Brain vitality is primarily a function of oxidative metabolism, and the predominant cause of neurological dysfunction and malfunction relates to the lack of sufficient brain oxidation, typically as a result of obstruction or otherwise insufficient arterial blood flow to the brain. Of course, this can occur even during surgery, and it has been estimated that at least 2,000 patients die each year in the United States alone due to anesthetic accidents, while numerous other such incidents result in brain damage of some degree; at the same time, certain major and complex surgical procedures, particularly of a neurological, cardiac or vascular nature, may require induced low blood flow or pressure conditions, which inevitably involves the potential of insufficient oxygen delivery to the brain. At the same time, the brain is the human organ which is most intolerant of oxygen deprivation, and brain cells will die within a few minutes if not sufficiently oxygenated. Moreover, such cells are not replaced, and thus involve irreversible brain damage which may potentially result in paralysis, disability, or even death.

Accordingly, the availability of immediate and accurate information concerning the state of brain oxygen saturation is of critical importance to anesthesiologists and surgeons, as well as other involved medical practitioners, particularly since the patients involved are typically in an unconscious state and thus unable to provide information by ordinary physical response. Up until the present time, however, the instrumentalities available for use, including such things as electroencephalograph ("EEG"), arterial pulse oximeter and blood pressure monitors, etc., and even invasive catheter monitoring of blood oxygen content, acidity, etc. by penetration of the jugular bulb (jugular vein) do not provide accurate, ongoing, timely (instantaneous) information as to cerebral (brain) blood oxygenation state, particularly since the brain blood supply is extensive, diffuse, pervasive, and largely venous in nature rather then arterial. Of course, it is also thus devoid of conventional pulsative characteristics essential to the operation of conventional oximeters.

Accordingly, such devices are not appropriate for cerebral usage, and of course they are typically made to be applied only to peripheral tissue or appendages in any event, i.e., a finger or an ear lobe, and are not utilized in conjunction with venous blood. Of course, jugular bulb catheters are highly invasive and relatively traumatic; at the same time, they merely provide blood samples which are removed and analyzed in another location, at a subsequent point in time, and thus only address the state of venous blood after it has left the brain.

BRIEF SUMMARY OF INVENTION

In a specific and particular sense, the present invention provides a spectrophotometric cerebral oximeter, which non-invasively and harmlessly provides accurate and continuous real-time information as to the oxygenation state of the human brain, on an in vivo basis, without attendant patient stress or discomfort of any nature. More broadly considered, the present invention provides in vivo spectrophotometric methods and apparatus adaptable to other relatively analogous biomedical procedures and functions, for monitoring oxidative metabolism and/or other physiologic function, condition, or state.

In the particular preferred embodiment disclosed, the invention provides an in vivo, spectrophotometric cerebral oximeter which will non-invasively provide continuous monitoring of cerebral oxidation, and will do so in a form and format of a nature immediately understandable and familiar to physicians, i.e., percent oxygen saturation. Further, the cerebral oximeter so provided operates by examining (sampling) the cerebral blood supply throughout the complete vascularization (arterial, venous, and capillary systems) within the area of investigation, and the particular region investigated is or may be selectively accessed in accordance with the invention, i.e., the tissue volume examined is regional in nature and of a generally predetermined extent and location, constituting less than the entire brain or other area. Still further, the apparatus and methodology in accordance with the invention includes the provision of a convenient and readily-usable sensor which may for example be used in a number of different locations, and/or moved from one location to another, for comparative consideration of the regions selectively accessed and examined, whether cranial or otherwise.

Accordingly, the cerebral oximeter in accordance with the invention examines, and measures, blood oxygen saturation (and thus, oxidative metabolism) in the entire array of blood vessels present in the cranial region being monitored, which in the brain may generally be considered as comprising (by volume) approximately 75 percent venous, 20 percent arterial, and 5 percent capillary. Thus, the cerebral oximeter provided in accordance with the invention addresses not only oxygen delivery via hemoglobin molecules moved arterially, but in addition addresses the general, overall state of cerebral oxygen consumption, which is of course directly related to brain vitality and state, and indicative of continued viability. As already indicated, the invention provides such information on an instantaneous real-time basis, and as a result provides critical immediate information capable of clearly and quantitatively indicating the need for urgent measures to provide increased or decreased cerebral oxygen supply or consumption (metabolic activity), momentary responses to which may well prevent serious neurological or other trauma or injury.

In addition, the cerebral oximeter or other such apparatus provided in accordance with the invention is convenient to use, non-invasive and non-traumatic, produces no attendant side effects, and provides specific, quantified information of a type not previously available. At the same time, such apparatus is compact and relatively portable in nature, may provide direct visible monitoring via CRT or other visual display, and provides digitally storable data which may readily be maintained for future review or comparison or printed out in hard copy, plotted, etc., and/or periodically accessed to provide ongoing trend data, for displaying or analyzing changes which occur over selected periods of time. As such, the apparatus may be used in such diverse circumstances as emergency or trauma conditions, whether in the field (at the scene of accidents, etc. for example) or in emergency medical centers, intensive care units, surgical operating rooms, hospital trauma centers, or at bedside, etc.

In particular, however, use during ongoing surgical procedures is clearly anticipated as satisfying an existing and important medical need, particularly during such procedures as brain surgery, open heart, organ or other transplant surgery, or that involving major blood vessels, for example, carotid endarterectomy; or other bypass surgery, etc., where blood flow is maintained through heart-lung machines and there is no arterial pulse present at all in the brain or body.

The foregoing major objectives, advantages and considerations of the invention, together with and including others, will become more apparent following consideration of the ensuing specification, particularly taken in conjunction with the appended drawings, briefly described hereinafter. Once again it is pointed out that the apparatus and methodology principally described hereinafter constitutes merely a preferred embodiment of the underlying invention, and does not specifically address other and further aspects thereof which will or may become further appreciated by those skilled in the art after consideration of the overall disclosure herein.

DESCRIPTION OF PREFERRED EMBODIMENTS

Figure 1:
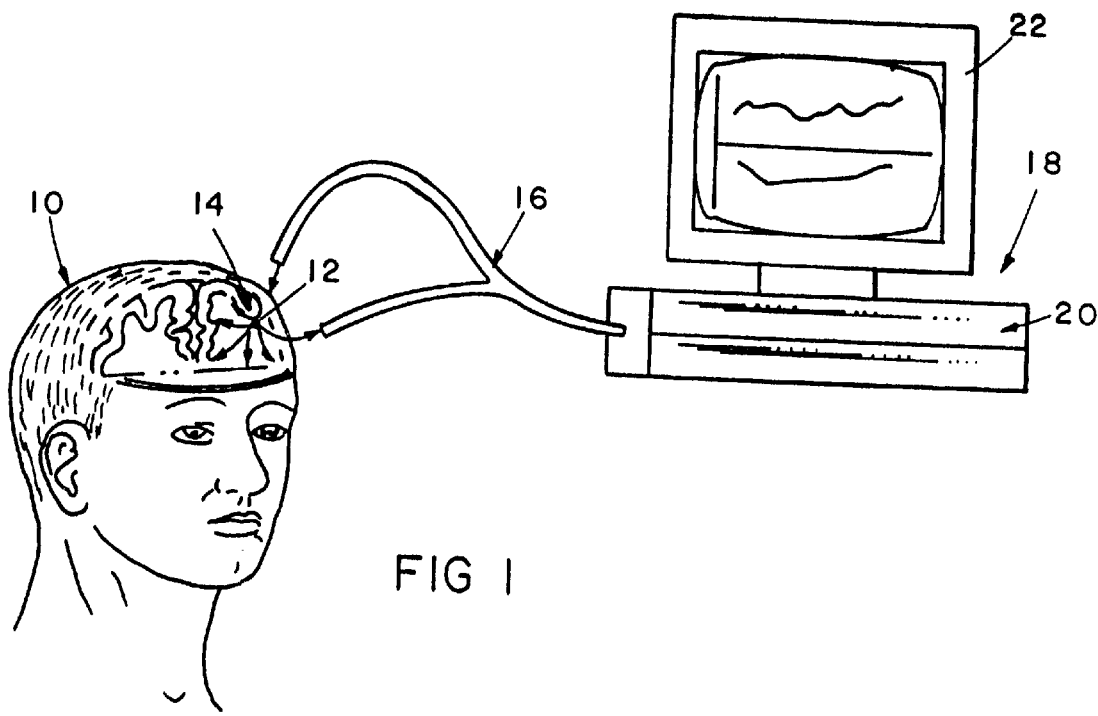
FIG. 1 is a pictorial schematic representation simplistically showing the basic application and utilization of apparatus in accordance with the invention.
Figure 2:
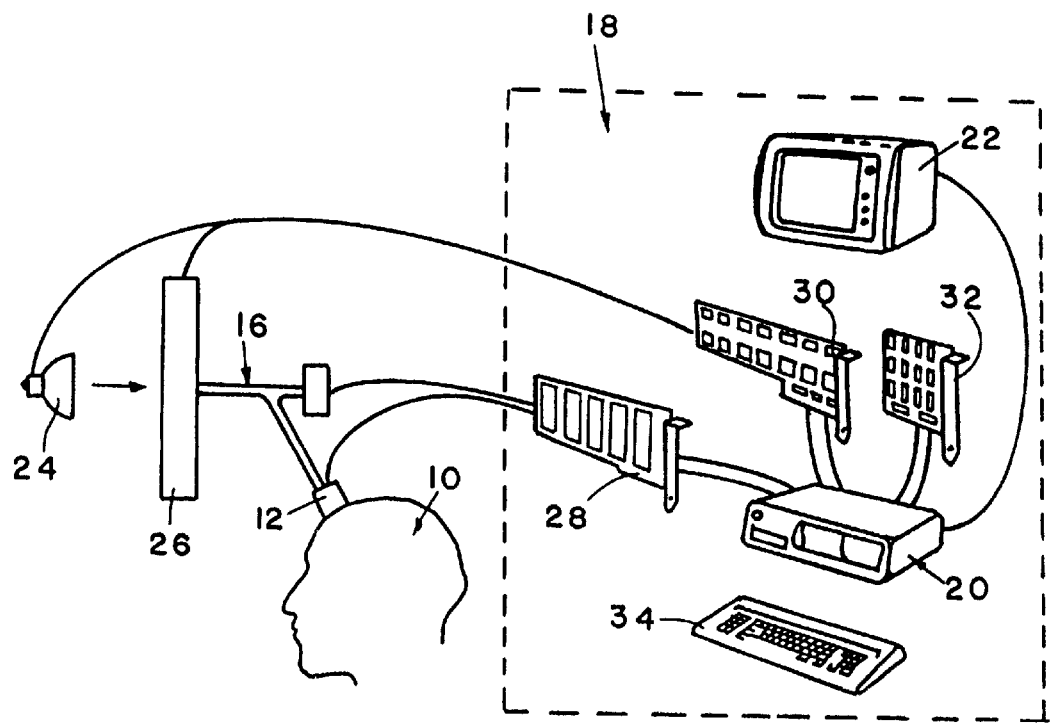
FIG. 2 is a further pictorial schematic representation somewhat similar to FIG. 1 showing additional aspects of the subject matter disclosed.

Oxygen is supplied to the brain by hemoglobin molecules contained in the blood supply, to which the oxygen molecules become bonded during the oxygenation process which occurs in the lungs as the blood is pumped by the heart through arteries and capillaries to the brain. As previously stated, the brain extracts oxygen from the hemoglobin by oxidative metabolism, and resulting carbon dioxide molecules are carried away through the capillaries and veins to the lungs for reoxygenation. Generally speaking, the optical spectrophotometry utilized by the invention is based upon the selective attenuation of particular light spectra in the near infrared range which is exhibited by oxygenated hemoglobin as compared to reduced (deoxygenated) hemoglobin contained in the blood present within the cerebral region under examination. FIGS. 1 and 2 pictorially and schematically show the overall or general application of the apparatus and methodology of the invention to the human cerebrum. Thus, FIGS. 1 and 2 show a human subject 10 upon whom apparatus in accordance with the invention is being utilized, such apparatus comprising a sensor means 12 for applying and receiving selected light spectra to a particular region 14 of the brain through or via conductors 16 (which, as subsequently noted, may be electrical or optical in nature), from or in conjunction with an infrared spectrophotometry unit 18 which includes in part a small digital computer 20 having a monitor 22 on which various forms of readout information may be presented. As generally shown in a pictorial and schematic manner by FIG. 2, the sensor assembly 12 applies selected light wavelengths which may emanate from a broadband source 24 (e.g., an incandescent lamp) and be selectively determined by narrow-bandwidth (monochromatic) filters 26, although as subsequently noted a preferred embodiment utilizes dedicated light-emitting diodes ("L.E.D.s") which produce the selected light spectra, and the computer 20 generally includes an A/D converter section 28, control circuitry 30 (depicted as a circuit board configured to mount in the expansion slots of computer 20), together with requisite computer memory 32 and an operator control in the form of a keyboard 34.

Figure 3:
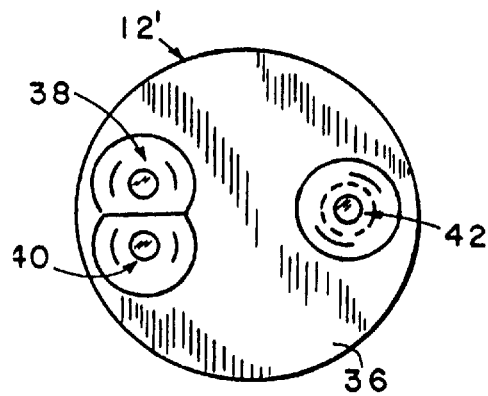
FIG. 3 is an end view of a first optical sensor assembly for use in conjunction with the invention.
Figure 5:
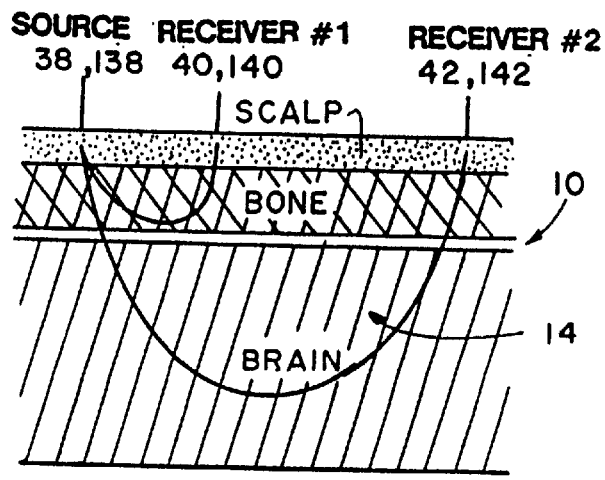
FIG. 5 is a schematic representation depicting the regional examination of the head and brain in accordance with the invention.
Figure 4:
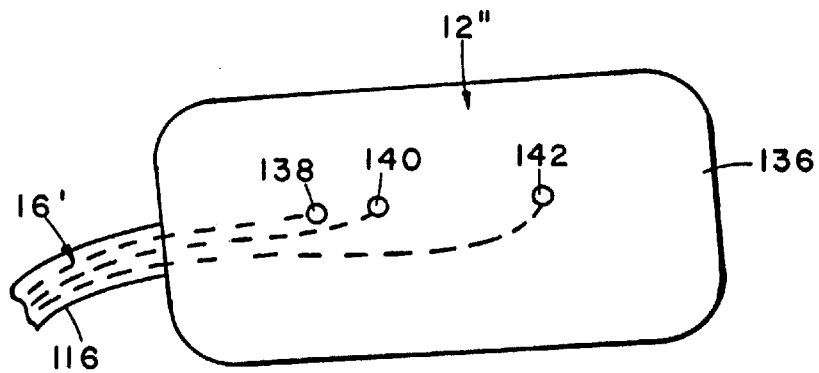
FIG. 4 is a pictorial side view representation of a different form of optical sensor, of a more preferred nature.

The sensor assembly 12 may as a general matter be in accordance with the above-referenced copending application Ser. No. 329,945 (the disclosure of which is incorporated herein by reference), one embodiment of which is shown for example in FIG. 3. Since described at length in the referenced copending application, it is neither necessary nor desirable to repeat such detailed description herein; however, it may be noted that, as shown in FIG. 3, such a sensor assembly 12' generally comprises a housing or other support 36 which carries a light-emitting element 38, a first light-detector or receiver 40 (i.e., the "near" receiver) and a second such detector or receiver 42 (the "far" receiver) which is disposed a predetermined and particular distance away from the source 38 and the "near" receiver 40. In the more preferred form generally depicted in FIG. 4 (and particularly disclosed and claimed in copending application Ser. No. 07/711,452, filed Jun. 6, 1991, incorporated herein by reference), the sensor assembly 12" is more elongated in overall shape and preferably has a somewhat flexible support 136 which carries the light source 138 and the near and far receivers 140, 142, respectively, all arranged in a longitudinal array, disposed along a common linear axis.

As noted, a complete and particular description of a sensor assembly corresponding to that shown at 12" is provided in the referenced copending and incorporated application; however, it may be noted that in this preferred form the source 138 comprises a pair of separate (but commonly-mounted) light-emitted diodes which provide at least two particularly-selected wavelengths (described in more detail subsequently herein), and the receivers 140 and 142 comprise photodiodes. As a result, the entire sensor assembly 12" is relatively small and compact, lightweight, and thin, as well as being at least modestly flexible; of course in this form the conductor array 16' comprises electrical conductors, since the operative elements are electro-optical emitters and detectors. Of course, such components operate with very low levels of electrical excitation, and the actual conductors 16' are each insulated from one another and carried within an insulating outer sheath 116.

Regardless of the particular form of sensor assembly 12 which is utilized, the inclusion and relative spacing of the source 38, 138, near receiver 40, 140, and far receiver 42, 142 are of great importance to the proper function and performance of apparatus in accordance with the invention, for the reasons set forth at length in the above-referenced and incorporated copending application Ser. No. 329,945. In general, however, the near receiver (40, 140) is close to but spaced a particular distance from the source (38, 138) so that the photons (light energy) which it detects in response to the emission of selected light spectra by the source will traverse primarily only the skin (scalp) and bone (skull) of the subject 10, whereas the "far" receiver (42, 142) is disposed a particular further distance from the source whereby the light energy (photons) which it receives samples a deeper tissue volume comprising primarily brain tissue. This selected brain tissue volume which is sampled, as generally delineated by the curving line designated 114 which illustratively depicts the mean optical path of the photons received at the far receiver 42, 142, constitutes the selected region 14 noted previously (FIG. 1), and it will be observed that such region constitutes a particular internal volume within the overall brain content whose location is determined by the relative disposition and separation of the source 38, 138, near receiver 40, 140, and far receiver 42, 142, together with the relative placement and location of the sensor assembly 12 upon the head of the subject 10.

Of course, there are practical limits to the maximum distance at which the far receiver (40, 140) may be disposed relative to the source (38, 138), since the level of light energy used must be less than that which would be harmful, while at the same time there must be more than merely trivial amounts of light energy received at the far receiver, in order to obtain meaningful data from the spectral modulation or attenuation of the light by the substance transmissed. As presently envisioned, it is probably not effective or useful to dispose the far receiver directly opposite (across the entire skull width) from the source, by which the complete width or diameter of the brain is transmitted, and it will be noted that in the configurations discussed above and depicted in the drawings, both the near and far receivers operate more in a "reflectance" mode than a "transmission" mode as those terms are conventionally used (i.e., they are disposed along mean optical paths which are curved, and are relatively close to the source). Of course, as already indicated, this is directly consistent with monitoring regional brain function, which represents the preferred embodiment of the invention. By way of example, in a particular such preferred embodiment the distance between the source and near receiver is approximately 0.3 inches, while the distance between the source and far receiver is approximately 1.0 inches; once again, however, reference is made to copending application Ser. Nos. 329,945 and 07/711,452, which are more directly related to this subject matter and contain more detailed disclosure.

Figure 6:
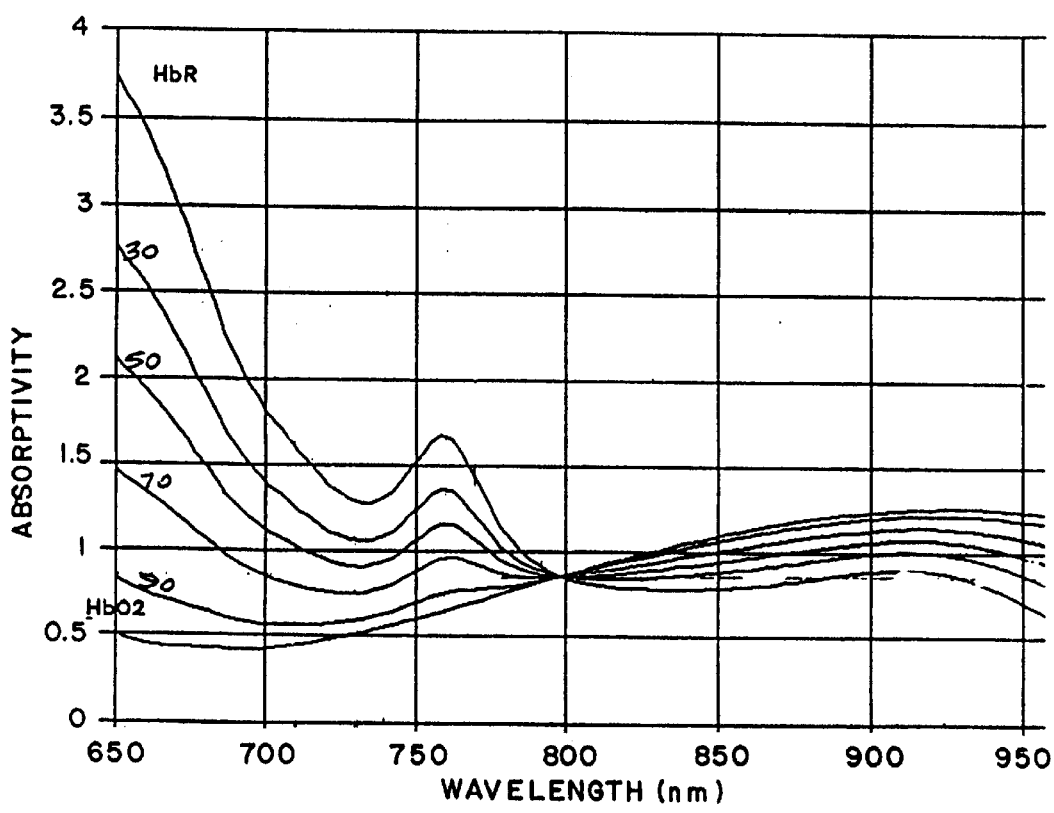
FIG. 6 is a graphical representation illustrating the spectral absorption characteristics of hemoglobin.

Generally speaking, some of the basic principles underlying the invention may be appreciated by reference to FIG. 6, which shows the known absorbtivity of hemoglobin to selected N.I.R. light wavelengths. As there illustrated, the spectral absorption characteristics of oxygenated hemoglobin describe a family of curves which intersect, and reverse, at a wavelength of approximately 800 nanometers ("nm"), which constitutes the isobestic point (typically considered to be at 815 nm). As illustrated, the absorbtivity of reduced (deoxygenated) hemoglobin rises progressively at lower wavelengths as a function of the relative absence of oxygen, the highest such curve thus representing fully deoxygenated hemoglobin and the lowermost such curve representing fully oxygen-saturated hemoglobin. As shown, these curves describe a peak in the general range of about 760 nm, as well as a valley or dip at approximately 730–740 nm. Accordingly, as is already known, by monitoring the optical response at selected wavelengths, i.e., by comparing intensity of light received at wavelengths less than the isobestic point with that received at the latter, and making appropriate computations, the oxygen content of sampled hemoglobin may be determined. In accordance with the invention, such sampling is preferably carried out at wavelengths representing points of most gradual change, rather than points representing steepest slopes; accordingly, a first sampling wavelength may be in the range of about 735 nm, and another may be at approximately 760 nm. Since the specific point at which isobestic conditions exist may vary somewhat as a result of a number of factors, the reference wavelength is preferably selected to be at approximately 805 nm.

In view of the foregoing, it will be appreciated that the primary focus of this description of preferred embodiments is based upon N.I.R. spectrophotometric procedures directed toward measurement of oxyhemoglobin and deoxyhemoglobin, in order to provide a cerebral oximeter as noted above, i.e., an apparatus for providing quantified information as to regional oxygen saturation in the composite vasculature of the brain, and the following further description sets forth mathematical descriptions and characterizations of the underlying rationale and procedure for such a device. It should be expressly noted, however, that the underlying invention is not necessarily limited to this specific application, and indeed is believed to have direct or meaningful application to other in vivo procedures which are or may be primarily attributed to or defined in meaningful part by other well-characterized chromophores, particularly (but not necessarily) in other somewhat analogous regional areas or domains, where information relative to biological processes in such a reasonably defined and distinctive area is important, and it is necessary or useful that such information be free of distortions attributable to hemoglobin or other attributes characterizing the skin, bone, and dura which is superficial to the more deeply-located region to be investigated.

With further and continuing reference to the particular preferred embodiment under discussion, it will be appreciated that the methodology of the invention utilizes diffused near-infrared spectroscopic procedures of a generally transmission-mode character for quantitative evaluation of tissue which is highly scattering and partially absorptive in nature, utilizing spatial resolution for region definition. Since wavelength-specific attenuation of light propagated through such tissue is a function of the chromophores, their extinction coefficients, their concentrations, and the distance photons travel in the tissue, the basic relationship may be analogized too, and expressed in accordance with, the Beer-Lambert relationship as set forth below, even though this is in fact deemed specifically descriptive of homogeneous non-scattering media:

$$I_{(w)} = I_{(w)0} e^{-sCa}$$

In the foregoing expression, the quantity $I_{(w)}$ represents intensity of transmitted light at wavelength w, the term $I_{(w)0}$ represents the intensity of the incident light at wavelength w, the term a represents the molar extinction coefficient of the light-absorbing molecule (chromophore), the term C represents the content of such chromophore in the tissue under examination, and the term s represents the photon pathlength in the tissue of interest. By use of this relationship, a fundamental approximation is obtained for interpreting the N.I.R. spectra utilized; since there are at least three significant chromophores present in brain tissue, each with separate extinction coefficients and concentrations, the above-noted relationship may be modified and expressed as follows;

$$\ln I_{(w)}/I_{(w)0} = \sum_{j=1}^{N} a_{(w,j)} C_{(j)} s$$

The measurements made at the selected examination wavelengths may be usefully referenced by subtracting them from reference measurements made at second selected wavelength i.e., the isobestic point of hemoglobin noted above in connection with FIG. 6. Since the above relationship refers to absorption at wavelength w, absorption at a second wavelength w' is subtracted from that at the first wavelength, w, yielding the following expression:

$$\ln I_{(w)}/I_{(w)0} + \ln I_{(w')}/I_{(w')0} = \sum_{j=1}^{N} (a_{[w,j]} - a_{[w',j]}) C_{(j)} s$$

The foregoing expression may be simplified by use of arbitrary definitions; i.e., everything directly measured may be defined by the variable M. Since the difference in extinction coefficient is also a known, it may be defined by the term d. Accordingly:

$$M_{(w)} = -\ln I_{(w)}/I_{(w)0} + \ln I_{(w')}/I_{(w')0}$$

$$d_{(w,j)} = a_{(w,j)} - a_{(w',j)}$$

Thus, the expression describing absorption at a second wavelength w' subtracted from that at a first wavelength w may be reduced to the following simpler notation:

$$M_{(w)} = \sum_{j=1}^{N} d_{(w,j)} C_{(j)} s$$

Consideration of the simplified relationship just expressed reveals that the variable of interest, chromophore concentration, may be quantified for oxyhemoglobin and deoxyhemoglobin if such expression is solved by making (N+1) measurements of M to solve for $c_{(j)}s$ (oxyhemogolbin) and $c_{(j)}s$ (deoxyhemogolbin) independently. These values are proportional to chromophore content. The value s is a constant, and by calculating the ratio of deoxy- to oxyhemoglobin, this constant cancels out of the expression. If this is assumed to be constant, the number of unknowns does not increase subsequent measurements, and this assumption appears to be well-supported. Thus:

$$C_{(j')}s/C_{(j)}s = C_{(j')}/C_{(j)} = Hr$$

In the foregoing expression, the variable Hr represents the hemoglobin ratio of deoxy- to oxyhemoglobin, which may then be used to solve for the regional saturation of hemoglobin designated $rSHgbo_2$ below:

$$1/(1+Hr) = Hbo_2/(Hgb+Hbo_2) = rSHgbo_2$$

It will therefore be seen that the term "$rSHgbo_2$", defined as "regional saturation of hemoglobin", constitutes the ratio of oxygenated hemoglobin to total hemoglobin in the sampled field (defined region) of the brain under investigation. As previously stated, this region will contain both arterial and venous blood, as well as a small capillary content, but the venous blood will heavily outweigh the arterial blood because the great majority (on the order of 70–80 percent) of the cerebral blood is in the venous compartment.

It will be appreciated that the foregoing relationship may be usefully implemented in computer software by appropriate algorithm, particularly in view of the comments and discussion set forth previously herein in conjunction with FIGS. 1–6 inclusive. In this regard, however, it is to be emphasized once again that the invention is preferably implemented by way of the preferred embodiments noted and the accompanying commentary; in particular, the transmitted light of wavelengths w, w', etc. is preferably sequentially applied in short bursts (pulses) by use of a suitable number of repetitions which alternate application of the selected wavelengths. Detection of resulting light for each such burst thus occurs at both the near and far locations essentially simultaneously, and is preferably obtained on a time-gated basis corresponding to the occurrence of the pulsed incident light wavelengths, providing synchronous detection/demodulation techniques. Of course, the detected light burst intensities at the selected wavelengths constitute an analog quantity as detected, and these are preferably converted to digital form for subsequent processing. The computer 20 noted in connection with FIGS. 1 and 2 is preferably utilized to control all time-based functions, as well as for the processing of digitized data in accordance with the aforementioned algorithm.

It should be expressly noted that differential processing (in essence, subtraction) of the near-far detection measurements is considered to be of the essence in order to define the selected internal region which is to be examined, and in particular to exclude the effects of the sampled near field from the measurements of the desired far field, thereby eliminating not only boundary (initial impingement and peripheral penetration) effects but also those attributable to transmission through the skin, bone and dura by the selected examination spectra. This processing may be carried out incrementally, prior to each iterative spectrophotometric transmission and detection sequence, since the digitized data may readily be stored on an increment-by-increment basis and used for further processing (or storage) as desired. It is believed useful, however, to accumulate an average for each particular type of measurement over a given number of cycles (i.e., bursts of investigative light at a common wavelength, received at a particular sensor), and then subtractively process the resulting averages in the manner just noted above.

It will be appreciated from the foregoing that the end result thus obtained will provide a quantified value for regional oxygen saturation of hemoglobin in the brain on an essentially instantaneous, real-time basis, which may be presented in various forms (e.g., as a numeric display on the computer monitor, updated at selected intervals or in accordance with other such parameters), or in a variety of other forms such as graphs, charts, etc. As an example of such formats, and to further illustrate the nature and value of information obtainable in accordance with the invention, reference is made to FIGS. 7–10, together with the following commentary pertaining thereto.

Figure 7:
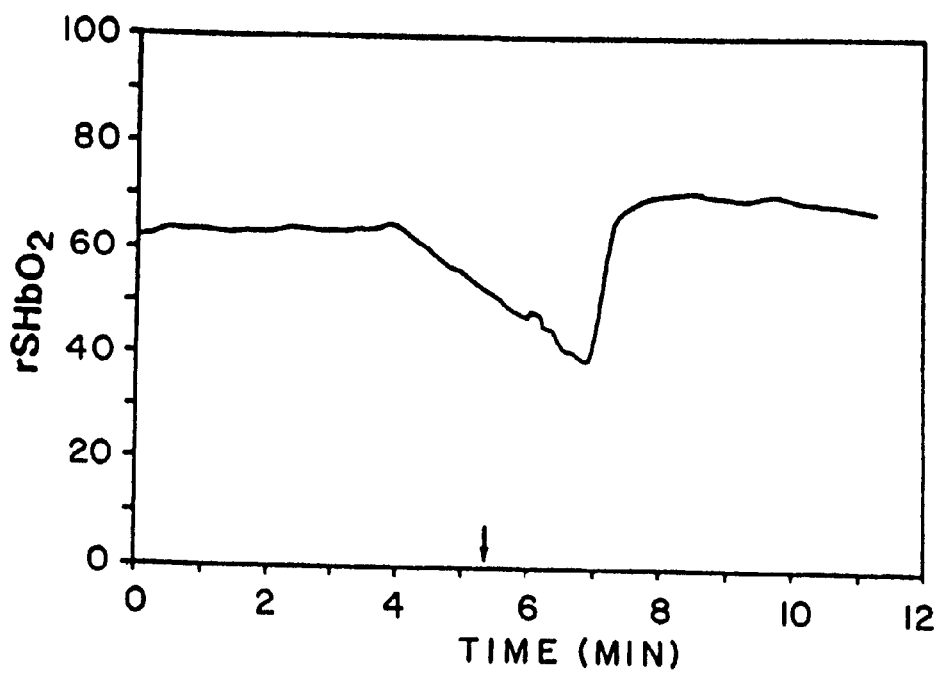
FIG. 7 is a graphical representation showing measured cerebral hemoglobin oxygen saturation in accordance with the invention in a first test subject.

FIG. 7 presents a graphical-form chart showing measured regional cerebral hemoglobin saturation with respect to time, obtained by actual clinical measurement of a human subject undergoing progressive cerebral hypoxia. As will be readily observed, a rapid shift from baseline to abnormal values (less than 55 percent) is clearly indicated, commencing at about the four minute point, as a result of the progressive hypoxia, as is the very rapid return to baseline (and in fact slightly elevated initial level exceeding baseline) following corrective patient respiration on one-hundred percent oxygen. Particular reference should be given to the arrow indicated on the abscissa scale, which indicates the point in time at which an analog EEG, retrospectively evaluated by a clinician on a "blind" basis, first indicated abnormal theta-delta activity. As may readily be seen from this, the clear indications of serious abnormality provided in accordance with the invention occurred well over a full minute before the earliest such EEG indication, and of course this occurs through ongoing, real-time quantified measurement in terms of percent oxygenation, whereas the EEG chart is retrospectively studied.

Figure 8:
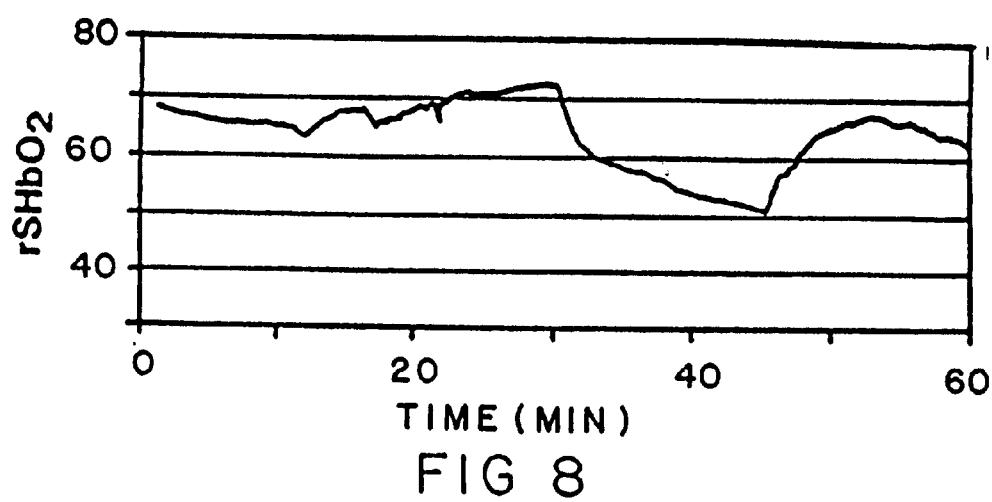
FIG. 8 is a graphical representation showing measured cerebral hemoglobin oxygen saturation in accordance with the invention in a second test subject.

FIG. 8 comprises a chart somewhat analogous to that presented in FIG. 7 and described above, but showing a longer-duration procedure during which the monitored patient underwent elective hypothermic cardiac standstill during surgical repair of a giant intracranial aneurysm. As will readily be noted, a clearly-perceptible decline from a baseline value in the range of 60–70 percent saturation commences at approximately 30 minutes, and extends to approximately 45 minutes, during which time the patient was completely off bypass and had no cerebral blood flow, and thus no oxygen delivery (under the aforementioned hypothermic conditions). Following reperfusion at approximately the 45 minute point, brain oxygen saturation is shown to rapidly return toward baseline, and may clearly be monitored during the highly important ensuing period.

Figure 9:
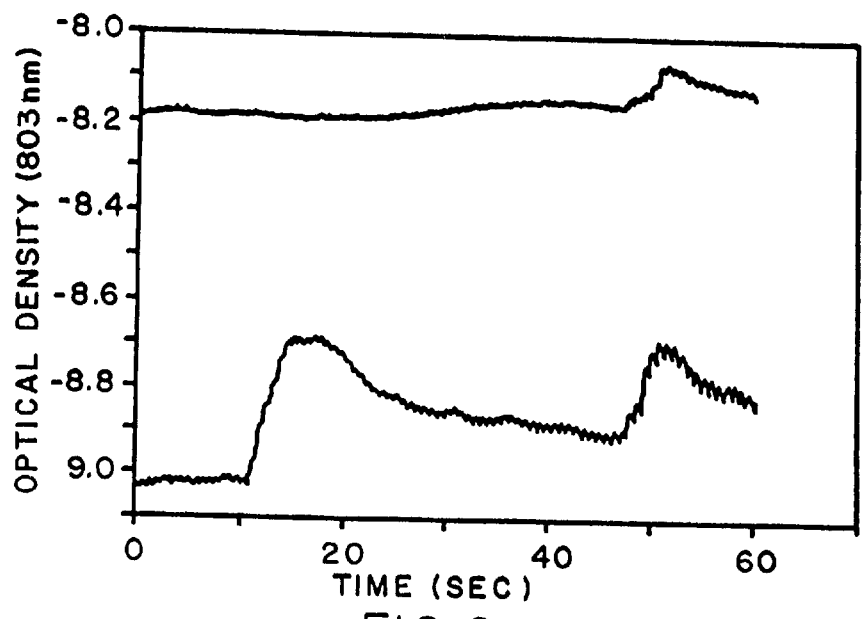
FIG. 9 is a graphical representation showing cerebral vascular oxygenation activity contrasted with extracerebral oxygenation of the scalp and skull, as measured by the near and far detectors provided in the sensor assembly utilized by the invention.

FIG. 9 comprises a different form of chart, presenting "optical density" (i.e., attenuative effect) at the reference wavelength over a period of time, in seconds, as evidenced by the detected light intensity information received separately at the near and far detector locations following introduction of a bolus of infrared tracer material. This chart thus shows transit of the tracer through the cerebral vasculature; that is, selective introduction of the tracer in the internal carotid artery results in initial presence thereof only in the deep tissue; thus, ipsilateral spectroscopic measurements made in accordance with the invention show (bottom trace) relatively immediate detection of the tracer at the "far" receiver monitoring the deeper brain tissue, without any attendant indication at the "near" receiver (upper trace) which monitors superficial tissue, etc., until substantially later, after the tracer has recirculated through the heart and entered the external carotid system, at approximately fifty seconds after the initial introduction of the tracer. In this regard, it will be noted that the far receiver also shows recirculation of the bolus at this second point in time, as well as graphically displaying the declining persistence of the tracer within the deep tissue over this interval.

Figure 10:
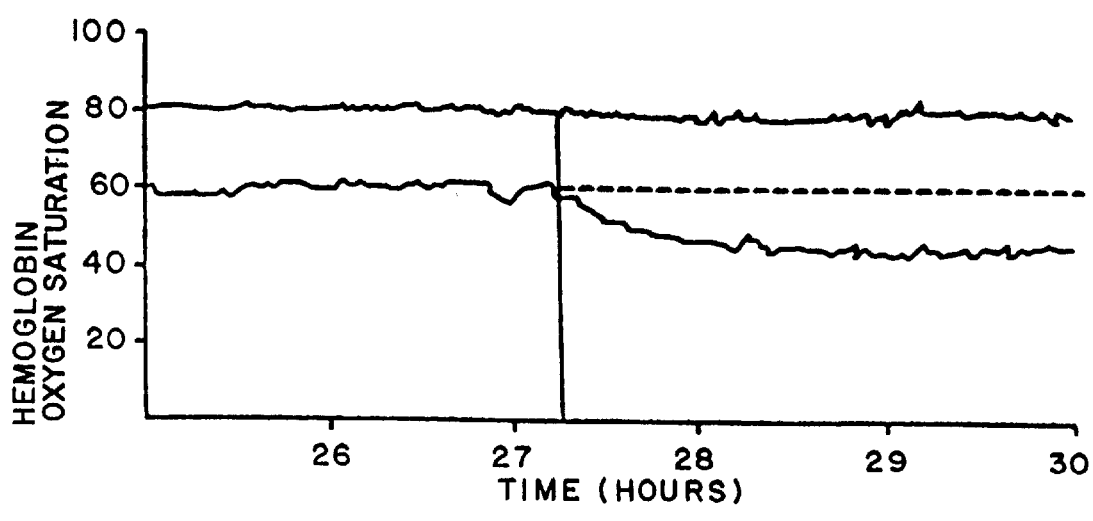
FIG. 10 is a further graphical representation showing cerebral oximetry measurements in accordance with the invention.

FIG. 10 constitutes a further graphical showing illustrative of the versatility, usefulness and value of information provided in accordance with the invention, by way of a pair of comparative traces showing (lower trace) continuous regional cerebral oxygen saturation (characterizing "deep", i.e., brain, tissue) as compared to that characterizing only the superficial tissue, i.e., scalp and skull (upper trace), an actual trauma patient who suffered a serious closed-head injury and was continuously monitored. As may readily be observed by noting the change occurring at the vertical line disposed at a point representing approximately 27.25 hours after the onset of monitoring, progressive cerebral desaturation commences notwithstanding the fact that the superficial blood supply remains fully oxygenated. It is to be noted that the first clinical manifestation of brain desaturation in this patient occurred more than two hours later, at approximately 29.5 hours.

From the foregoing, the significance and value of information provided in accordance with the invention is believed readily apparent, corroborating expectations based upon appreciation of the fact that cerebral venous oxygen saturation should constitute an excellent indicator of the adequacy of cerebral oxygen delivery and/or cerebral oxygen extraction, and thus of brain vitality as a general matter. That is, cerebral oxygen extraction causes rapid changes in cerebral venous oxygen saturation when cerebral oxygen delivery decreases for any reason, as for example the presence of systemic hypoxia, cerebral oligemia, systemic anemia, etc., even though cerebral oxygen consumption may remain normal. In this regard, the very advantageous results obtained through the spatial resolution techniques noted, providing for specific and independent monitoring of information from deep vascular beds or tissue, provides for desirable organ-specific or area-specific determinations made well below the skin. Further, although the specific accuracy and sensitivity of oximetry measurements in accordance with the invention in heterogeneous tissue such as the scalp and adjacent or near underlying area remain to be seen, and potentially further defined, the usefulness of the resulting information is clearly demonstrated by examples such as those presented in FIGS. 9 and 10, as discussed above.

As for specific accuracy of regional oxygen saturation determinations pursuant to the mathematical paradigm set forth above, comparative evaluation may readily be accomplished for any specific implementation, and has in fact been done by use of in vitro human blood which was suitably warmed and artificially oxygenated to various saturations, and then subjected to comparative testing with a standard lab cooximeter (using a customized cuvette with immersible light guides for access by apparatus in accordance with the invention). By utilizing linear regression analysis, highly significant correlation is shown which supports the underlying soundness of the mathematical approach discussed above. Of course, appropriate scale factors may be determined in this general manner for any desired specific application of the methodology disclosed herein, and used to calibrate or correlate the actual output of the implemented apparatus, for example by conventional computer data-processing techniques such as embodying the scale factors in appropriate look-up tables, for example. It may be noted that such procedures may also provide a desirable or useful calibration technique in any event.

It should be further pointed out that since the quantified values of regional hemoglobin oxygen saturation provided in accordance with the invention constitute field values, i.e., represent hemoglobin contained in three separate vascular compartments (arterial, venous and microcirculatory), these quantified values represent the weighted average of the three different vascular compartments. While hydraulic analysis of the cerebral vascular system, as evidenced by published information, supports a cerebral blood volume distribution that is in accordance with that set forth above, it may be noted that the specific relative size of each such blood volume compartment is in fact dynamic in a given patient depending upon the ratio of oxygen supply to and demand during conditions of physiologic stress, anatomic location, and in numerous other factors; consequently, an ideal reference methodology would simultaneously measure the actual relative blood volume of these three different compartments, preferably on a regional basis. Nonetheless, employment of assigned weighting values in the mathematical paradigm used, pursuant to the published hydraulic or other analytic information available, is quite sufficient for purposes of providing useful clinical instrumentation. Of course, the presence of extravascular cerebral blood collection, for example in the subarachnoid, subdural, or intraparenchymal tissue compartments, could or may potentially interfere with the strict accuracy of the quantifications provided, even though relative or trend data based thereon would seemingly still be of considerable importance; further, the spatial resolution capabilities of the invention may in fact provide a way to comparatively assess such anomalies, particularly if they are reasonably well defined. At the same time, the paradigms set forth above, being primarily designed to measure and account for extraparenchymal conditions, have the potential to overcome such problems.

Accordingly, it is believed that a highly useful and novel methodology is provided by the invention, particularly, but certainly not exclusively, as applied in the preferred embodiment discussed herein above, as well as in other related or analogous applications. It is to be understood that the foregoing description of a preferred embodiment of the invention is provided for purposes of description and illustration, and not as a measure of the invention, whose scope is to be defined solely by reference to the ensuing claims. Thus, while those skilled in the art may devise embodiments of the particular concepts presented in the foregoing illustrative disclosure which differ somewhat from the particular embodiment shown and described in detail herein, or may make various changes in structural details to the illustrated embodiment, all such alternative or modified embodiments which utilize the concepts of the invention and clearly incorporate the spirit thereof are to be considered as within the scope of the claims appended herebelow, unless such claims by their language specifically state otherwise.

The embodiments of the invention in which an exclusive property or privilege is claimed are defined as follows:

1. A spectrophotometric cerebral instrument suitable for conducting in vivo clinical examinations, comprising in combination:

means for applying selected spectra in the near infrared range to the head of a patient at a first location so that they transmiss at least selected portions of the brain after entry through the scalp and skull, said spectra including at least one reference wavelength and at least one investigative wavelength;

means for receiving light energy resulting from said applied spectra at second and third selected locations on the outside of said skull after said applied spectra have passed through said selected brain portions, said second and third locations being spaced from said first location by different distances;

means for producing corresponding and representative signals from the light energy received at said second and third locations;

and means for processing said signals by contrasting certain of said signals representative of light energy corresponding to said reference wavelength and received at said second location with signals representative of light energy corresponding to said investigative wavelength received at said second location to obtain a first resultant signal, contrasting certain of said signals representative of light energy corresponding to said reference wavelength received at said third location with signals representative of light energy corresponding to said investigative wavelength received at said third location to obtain a second resultant signal, and then contrasting said first and second resultant signals, to produce an output which is directly indicative of a predetermined regional cerebral pathology condition in said portion of said brain.

2. A spectrophotometric instrument according to claim 1, including means for producing a visual readout from said output which is indicative of cerebral blood oxygenation.

3. A spectrophotometric instrument according to claim 2, wherein said readout is in terms of hemoglobin oxygen saturation.

4. A spectrophotometric instrument according to claim 2, wherein said means for processing said signals operates to contrast certain of such signals by subtracting certain of said logarithm equivalents from one another.

5. A spectrophotometric instrument according to claim 1, including means for processing said signals by producing logarithm equivalents of the signals received at said second and third locations prior to said contrasting of signals.

6. A spectrophotometric instrument according to claim 1, wherein said means for applying, receiving and processing function cooperatively such that said readout characterizes the blood oxygen content of a selected region of said brain.

7. A spectrophotometric instrument according to claim 6, wherein said output comprises a calculated composite indicator representative of the oxygen content of each of the different types of blood within said region.

8. A method of determining cerebral blood oxygenation by in vivo optical spectrophotometry comprising the steps of: applying selected light spectra in the near infrared range to the head of a patient at a first location so as to transmit portions of the brain through the scalp and skull; receiving light energy resulting from and corresponding to said applied spectra at second and third selected locations on the outside of said skull, each spaced from one another and from said first location; producing corresponding signals representative of the light received at both said second and third locations; and processing said signals to produce therefrom a readout which is indicative of cerebral blood oxygen saturation in at least portions of said brain transmissed by said light spectra; said processing including the steps of contrasting certain of said signals representative of light energy corresponding to a selected wavelength received at said second location with signals representative of light energy corresponding to another selected wavelength received at said third location to obtain a first resultant signal having a value which is proportional to the ratio of deoxygenated hemoglobin with respect to oxygenated hemoglobin in at least said portions of said brain, and then using the value of said resultant signal to compute a further resultant signal having a value which is proportional to the ratio of oxygenated hemoglobin with respect to the sum of oxygenated hemoglobin and deoxygenated hemoglobin, said further resultant signal being indicative of cerebral blood oxygen saturation in said at least portions of said brain transmissed by said light spectra.

9. The method according to claim 8, wherein said signal-processing step is carried out by producing logarithmic equivalents of said signals representative of light received at said second and third locations prior to performing at least some of said signal-contrasting steps, whereby said contrasting steps are carried out by using said logarithmic equivalents.

10. The method according to claim 9, wherein at least some of said signal-contrasting steps in said signal-processing comprise subtracting certain of said logarithmic equivalents from one another.

11. The method according to claim 8, including the steps of selecting said first location as one where the scalp and skull overlie a plurality of said differently oxygenated types of blood, applying said selected spectra to transmit each of said blood types, and processing said signals produce a readout which characterizes a selected composite of said differently oxygenated types of blood.

12. The method according to claim 8, including the step of processing said signals to produce a readout which characterizes a defined region of said brain.

13. The method according to claim 8, including the step of producing said readout as a visible display.

14. The method according to claim 13, including the step of producing said readout as a numeric display.

15. The method according to claim 13, including the step of producing said readout as a graph-form display.

16. The method according to claim 15, wherein one axis of said graph-form display is a time representation, whereby said display shows trend data.

17. The method accordingly to claim 8, including the step of producing said readout in terms of cerebral blood oxygen saturation.

18. The method according to claim 17, including the step of producing said readout in terms of percent hemoglobin oxygen saturation.

19. A method of determining cerebral blood oxygenation by in vivo optical spectrotometry comprising the steps of: applying selected light spectra in the near infrared range to the head of a patient so as to transmiss portions of the brain through the scalp and skull and to transmiss the overall vasculature present within said brain portions, including each of the various types of blood supply present within at least said brain portions, whether arterial, venous or capillary in nature; receiving light energy resulting from and corresponding to said applied spectra at selected locations on the outside of said skull, and producing corresponding and representative signals therefrom; and processing said signals in a manner to produce a readout which is indicative of the oxygen content of a composite of the total blood supply in said overall vasculature by calculating an average representative of the oxygen content present in all of said types of blood supply present within said brain portions and calculating a weighted average based upon said representative average and upon an assumed relative blood volume present for each of said different types of blood supply present within said brain portions.

\* \* \* \* \*